United States Patent [19]

Strike

[11] 3,972,917
[45] Aug. 3, 1976

[54] 11-DEOXY 15-METHYL PROSTAGLANDIN $E_1$

[75] Inventor: Donald P. Strike, Philadelphia, Pa.

[73] Assignee: American Home Products Corporation, New York, N.Y.

[22] Filed: May 28, 1974

[21] Appl. No.: 473,604

Related U.S. Application Data

[63] Continuation of Ser. No. 301,571, Oct. 27, 1972, abandoned.

[52] U.S. Cl. ............... 260/514 D; 260/247.2 R; 260/268 R; 260/293.6 S; 260/326.2; 260/340.4; 260/468 D; 260/501.1; 260/501.17; 424/30; 424/317

[51] Int. Cl.² .................. C07C 61/38; C07C 69/74

[58] Field of Search .............. 260/468 D, 514 D

[56] References Cited

UNITED STATES PATENTS

| | | | |
|---|---|---|---|
| 3,671,570 | 6/1972 | Bagli et al. | 260/468 |
| 3,729,502 | 4/1973 | Beal | 260/468 |
| 3,816,393 | 6/1974 | Hayashi | 260/209 R |
| 3,873,607 | 3/1975 | Bernardy et al. | 260/514 |

FOREIGN PATENTS OR APPLICATIONS

| | | | |
|---|---|---|---|
| 2,334,522 | 1/1974 | Germany | 260/468 |

*Primary Examiner*—Robert Gerstl
*Attorney, Agent, or Firm*—Robert Wiser

[57] ABSTRACT

11-Deoxy-prostaglandin compounds having a lower alkyl group at position-15 are prepared from $PGA_2$ esters and 15-epimers. These 15-lower alkyl-11-deoxy prostaglandins possess bronchodilative ability.

3 Claims, No Drawings

11 DEOXY 15-METHYL PROSTAGLANDIN E₁

This is a continuation of application Ser. No. 301,571 filed Oct. 27, 1972, now abandoned.

BACKGROUND OF THE INVENTION

The prostaglandins are a group of hormone-like substances whcih may be viewed as derivatives of prostanoic acid. Several prostaglandins are found widely distributed in mammalian tissue and have been isolated from this source. These prostaglandins have been shown to possess a variety of biological properties such as bronchodilation, the ability to reduce gastric secretion, to modify muscle tone, as well as the ability to raise or lower blood pressure.

Various derivatives of prostaglandins have also been synthesized and reported. U.S. Pat. No. 3,671,570 describes completely saturated prostaglandin compounds having a lower alkyl group in the 15-position. Netherlands specification No. 68,16804 and South African Pat. No. 66/3600 describe the compound, 11-deoxy-PGE₁.

SUMMARY OF THE INVENTION

The invention sought to be patented in its composition aspect, resides in the concept of a chemical compound of the structure

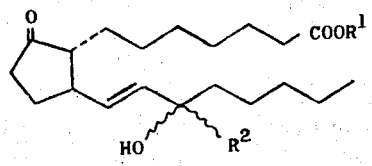

wherein $R^1$ is hydrogen, alkyl of from 1 to about 6 carbon atoms, alkali metal, or a pharmacologically-acceptable cation derived from ammonia or a basic amine, and $R^2$ is alkyl of from 1 to about 6 carbon atoms.

The tangible embodiments of the composition aspect of the invention possess the inherent general physical properties of being clear to yellow oils or solids; their solubility will vary according to the nature of the group $R^1$. Where $R^1$ is hydrogen, or alkyl they are substantially insoluble in water and soluble in organic solvents such as ethyl acetate and ether. Where $R^1$ is other than hydrogen or alkyl, there is increased water solubility, with a concomitant decrease in organic solvent solubility. Examination of compounds produced according to the hereinafter described process reveals, upon infrared, nuclear magnetic resonance, and mass spectrographic analyses, spectral data supporting the molecular structures herein set forth. The aforementioned physical characteristics, taken together with the nature of the starting materials, the mode of synthesis, and the elemental analysis, confirm the structure of the compositions sought to be patented.

The tangible embodiments of the composition aspect of the invention possess the inherent applied use characteristic of exerting bronchodilating effects upon administration to warm-blooded as evidenced by pharmacological evaluation according to standard test procedures.

The invention sought to be patented in its process aspect resides in the concept of a method of relieving bronchial spasm and facilitating breathing in warm-blooded animals which comprises administering to a warm-blooded animal in need thereof an amount sufficient to relieve bronchial spasm and facilitate breathing in said warm-blooded animal of a composition comprising:

a. a compound of the formula

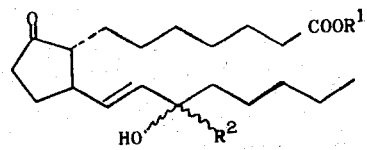

wherein $R^1$ is hydrogen, alkyl of from 1 to about 6 carbon atoms, alkali metal, or a pharmacologically-acceptable cation derived from ammonia or a basic amine, and $R^2$ alkyl of from 1 to about 6 carbon atoms; and b. a pharmacologically-acceptable carrier.

DESCRIPTION OF THE PREFERRED EMBODIMENTS

In describing the invention, reference will be made to the following schematic illustration of the reaction sequence for preparing a specific embodiment thereof, wherein compounds are assigned Roman numerals for identification.

The starting material (II) in a preferred synthesis of the compounds of the invention is 15-epi-PGA₂, methyl ester, acetate, which may be isolated from the coral *Plexaura homomalla* [Weinheimer and Spraggins, Tetrahedron Letters, 59, 5185 (1969)].

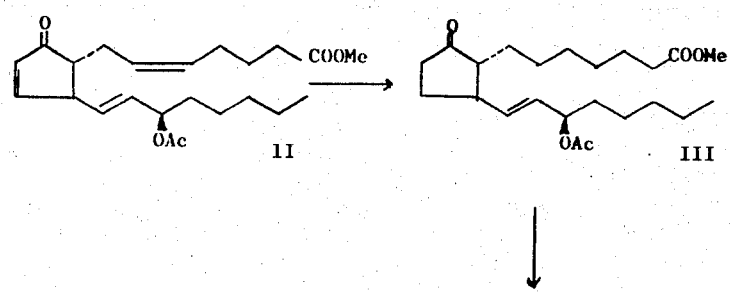

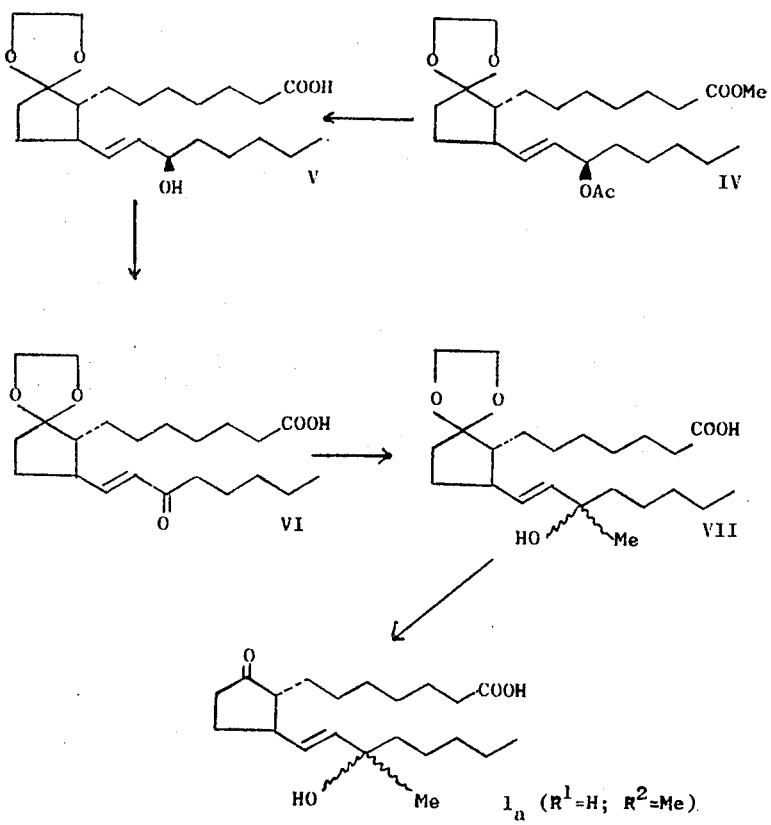

Hydrogenation of II in the presence of tris(triphenylphosphine)-rhodium (I) chloride affords the corresponding mono-ene compound (III), which is then ketolized by art-recognized means, for example by treatment with ethyleneglycol in the presence of an organic acid such as p-toluenesulfonic acid, to form the corresponding ketal (IV). Basic hydrolysis of IV affords the hydroxy-acid V. Oxidation of V with Jones reagent yields the corresponding 15-ketone compound (VI), which on treatment with alkyl grignard reagent, for example methyl magnesium bromide, gives the 15-methyl-15-hydroxy compound (VII). Deketalization of VII, for example with perchloric acid in tetrahydrofuran affords the compound of the invention I.

Although the reaction was above-described with reference to an embodiment of the invention wherein $R^2$ is methyl, it will be apparent to one skilled in the art of chemistry that the various embodiments wherein $R^2$ is other than methyl may be readily synthesized by use of the appropriate grignard reagent.

It will be apparent to those skilled in the art of chemistry that the carbon atom to which substituent $R^2$ is attached is an asymmetric carbon atom, and as a consequence this position can be in either of two epimeric configurations. Substituent $R^2$ is introduced in the preparation of the compounds of the invention and its introduction results in the formation of a mixture of both epimeric forms with reference to that position. The symbol ⌇⌇⌇ where used in the formulae of this application is to indicate that both forms are intended and are included within the scope of the invention. If desired, of course, one could separate epimeric mixtures by various means well-known in the art, such as chromatography.

The esters of formula I ($R^1$ is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of the invention can be prepared by mixing stoichiometrically equivalent amounts of the free acids of formula I, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "alkyl of from 1 to about 6 carbon atoms" when used herein and in the appended claims includes straight and branched hydrocarbon radicals, illustrative members of which are methyl, ethyl, n-propyl, i-propyl, n-butyl, t-butyl, n-pentyl, n-hexyl, 3-methylpentyl, 2,3-dimethylbutyl, and the like. "Alkali metal" includes, for example, sodium, potassium, lithium and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

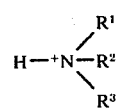

wherein $R^1$, $R^2$, and $R^3$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylhydroxyalkyl of from about 7 to about 15 carbon atoms or, when taken together with the nitrogen atom to which they are attached, any two of $R^1$, $R^2$, and $R^3$ from part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethylidiethanolammonium, n-butylmonoethanolammonium, tris(hydroxymethyl)methylammonium, phenylmonoethanolammonium, and the like.

In practicing the method of the invention, the instant compositions can be administered in a variety of dosage forms, the oral route being used primarily for maintenance therapy while injectables tend to be more useful in acute emergency situations. Inhalation (aerosols and solution for nebulizers) seems to be somewhat faster acting than other oral forms but slower than injectables and this method combines the advantages of maintenance and moderately-acute stage therapy in one dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example a hand nebulizer or a pressurized aerosol dispenser the dose is from about 5 micrograms to about 100 micrograms, and preferably from about 10 to about 50 micrograms, approximately every 4 hours, or as needed. By the oral ingestion route, the effective dose is from about 1 to about 20 mg., preferably from about 5 to about 15 mg. up to a total of about 40 mg. per day. By the intravenous route, the ordinarily effective dose is from about 50 micrograms to about 300 micrograms, preferably about 200 micrograms per day.

For unit dosages, the active ingredient can be compounded into any of the usual oral dosage forms incuding tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart bronchodilating activity thereto. This will range upward from about 0.0001% by weight of active ingredient in said composition.

For administration by the oral inhalation route with conventional nebulizers or by oxygen aerosolization it is convenient to provide the instant active ingredient in dilute aqueous solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture or dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. Nos. 2,868,691 and 3,095,355, for example.

The following examples further illustrate the best mode contemplated by the inventor of carrying out the invention:

EXAMPLE 1

2-(3-Hydroxy-1-Octenyl)-5-Oxocyclopentaneheptanoic Acid, Methyl Ester, Acetate

A solution of 5.0 g. of 15-epi-PGA$_2$, methyl ester, acetate and 1.125 g. of tris-(triphenylphosphine)rhodium (I) chloride in 300 ml. of 1:1 benzene-ethanol was hydrogenated until 2 equivalents of hydrogen were absorbed at 25°C. and atmospheric pressure. Evaporation of the solvent and silica chromatography of the residue with 20% ethyl acetate-hexane gave 3.4 g. of the title product, $\lambda_{max}^{film}$ 3.35, 5.65, 7.25, 8.0, 9.75, 10.3 $\mu$. NMR: $\delta$ 5.65 (M, 2, 13 and 14-H), 5.32 (M, 1, 15-H), 3.70 (s, 3, OCH$_3$), 2.05 (S, CO—CH$_3$) ppm.

Calcd. for $C_{23}H_{38}O_5$: C, 70.01; H, 9.71. Found: C, 70.31; H, 9.51.

EXAMPLE 2

7-(3-Hydroxy-1-Octenyl)-1,4-Dioxaspiro[4.4]Non-6-Ylheptanoic Acid, Methyl Ester, Acetate A solution of 3.6 g. of 2-(3-hydroxy-1-octenyl)-5-oxo-cyclopentane heptanoic acid, methyl ester, acetate and 0.15 g. of p-toluene-solfonic acid in 150 ml. of benzene and 15 ml. of ethylene glycol was relfuxed with a water separator for 20 hours. The reaction mixture was cooled, diluted with ether, washed with water and dried. Evaporation of the solvent gave 3.85 g. of the title product, $\lambda_{max}^{film}$ 3.45, 5.70, 7.30, 8.05, 9.70, 10.30, 10.55 $\mu$. NMR: $\delta$ 3.92 (s, ketal), 3.68 (S, OCH$_3$), 2.05 (S, CO—CH$_3$) ppm.

EXAMPLE 3

7-(3-Hydroxy-1-Octenyl)-1,4-Dioxaspiro[4.4]Non-6-Ylheptanoic Acid

A solution of 3.85 g. of 7-(3-hydroxy-1-octenyl)-1,4-dioxaspiro[4.4]non-6-ylheptanoic acid, methyl ester, acetate in 75 ml. of methanol was treated with 75 ml. of 1N sodium hydroxide and kept at 25° for 0.5 hours. The reaction mixture was diluted with water, washed with ether, acidified with acetic acid and extracted with ether. After washing and drying, the ether extract was evaporated and the residue chromatographed on silica. Elution with 50% ethyl acetate-hexane afforded 0.94 g.

of the title product, $\lambda_{max}^{film}$ 3.0 (shoulder), 3.4, 5.75, 6.85, 8.75, 9.25, 10.4 $\mu$. NMR: 6.35 (S, 2, OH), 5.52 (M, 2, 13 and 14-H), 4.05 (M, 1, 15-H), 3.92 (S, 4, ketal) ppm.

Calcd. for $C_{22}H_{38}O_5$: C, 69.07; H, 10.01. Found: C, 69.01; H, 10.29.

EXAMPLE 4

7-(3-Oxo-1-Octenyl)-1,4-Dioxaspiro[4.4]Non-6-Ylheptanoic Acid

A solution of 0.75 g. of 7-(3-hydroxy-1-octenyl)-1,4-dioxaspiro[4.4]non-6-ylheptanoic acid in 40 ml. of acetone was cooled to 0°C. and treated with 2.0 ml. of Jones Reagent. After stirring for 10 minutes, at 0°C., the reaction mixture was treated with 5 ml. of methanol, dilute sodium bicarbonate until basic and water. Following acidification with acetic acid, the mixture was extracted with ether and the extract washed with water, dried and evaporated. Silica chromatography of the resulting residue with 30% ethyl acetate-hexane gave 0.355 g. of the title product, $\lambda_{max}^{film}$ 3.1 (shoulder), 5.8, 6.1, 6.75, 8.6, 9.6, 10.1, 10.5 $\mu$. NMR: $\delta$ 6.78 (dd, 1, J=8.3, 15.8, 13-H), 6.18 (d, 1, J-15.8, 14-H), 3.92 (S, 4, ketal) ppm. UV: $\lambda_{max}^{EtOH}$ 230 m$\mu$ ($\epsilon$ 10,000). Mass spectrum $M^+$ at m/e 380.2523 (theory 380.2562).

EXAMPLE 5

2-(3-Hydroxy-3-Methyl-1-Octenyl)-5-Oxocyclopentaneheptanoic Acid

A solution of 0.235 g. of 7-(3-oxo-1-octenyl)-1,4-dioxaspiro[4.4]non-6-ylheptanoic acid in 20 ml. of tetrahydrofuran was cooled to 0°C. and treated with 1.32 ml. of 3M methyl magnesium bromide in ether. After stirring at 0°C. for 0.5 hours, the reaction mixture was diluted with ammonium chloride solution, acidified with acetic acid and extracted with ether. The extract was washed, dried and evaporated to obtain 0.222 g. of crude 7-(3-hydroxy-3-methyl-1-octenyl)-1,4-dioxaspiro[4.4]non-6-ylheptanoic acid.

The above crude product was dissolved in 9 ml. of tetrahydrofuran and 2.1 ml. of 3M perchloric acid and stirred at 25°C. for 22 hours. The reaction mixture was diluted with ether, washed, dried and evaporated. Silica chromatography of the residue with 30% ethyl acetate-hexane afforded 0.076 g. of the title product, $\lambda_{max}^{film}$ 2.95, 3.5, 5.75, 6.9, 8.6, 10.3 $\mu$. NMR: $\delta$ 5.88 (S, OH), 5.62 (M, 13 and 14-H)ppm. Mass spectrum: $M^+$ at m/e 352.2660 (theory 352.2613).

EXAMPLE 6

Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine (ACH) was administered at doses of 10 to 40 mcg./kg. depending on each animal's sensitivity to this compound, and control responses to acetylcholine were thus established. Bronchoconstrictor agents raise the resistance of the lungs to inflation thereby decreasing the tidal air flow. 2-(3-Hydroxy-3-methyl-1-octenyl)-5-oxocyclopentaneheptanoic acid was then administered by aerosol, and the animals were then challenged again with acetylcholine, and the degree of inhibition of bronchoconstriction was thus determined. A minimum of two animals was used at each dose.

Results

| Total Aerosol Dose (mcg.) | Mean % Protection VS ACH Bronchoconstriction |
|---|---|
| $1.5 \times 10^{-4}$ | 14 |
| $1.5 \times 10^{-3}$ | 52 |
| $1.5 \times 10^{-2}$ | 74 |
| $1.5 \times 10^{-1}$ | 83 |

EXAMPLE 7

A composition is prepared comprising 1 part of 2-(3-hydroxy-3-methyl-1-octenyl)-5-oxocyclopentaneheptanoic acid and 300 parts by weight of 0.06 M aqueous phosphate buffer. For administration to relieve bronchial spasm by oral inhalation with a hand nebulizer, in animals from about 20 to about 80 kilograms body weight, 3 to 5 inhalations of the solution are used every 4 hours.

EXAMPLE 8

The procedure of U.S. Pat. No. 2,868,691 is used to prepare compositions in self-propelling dosage unit forms.

"A suitable measured quantity of the medicament is mixed with, and dissolved in, a measured amount of the cosolvent. A stabilizer, if desired, is added. A measured quantity of the resulting solution is then introduced into an open container. The open container and its contents are then cooled, preferably to a temperature below the boiling point of the propellant to be employed. A temperature of −25°F. is usually satisfactory. A measured quantity of the liquified propellant which also has been cooled below its boiling point is then introduced into the container and mixed with the solution already present. The quantities of the components introduced into the container are calculated to provide the desired concentration in each of the final compositions. Without permitting the temperature of the container and its contents to rise above the boiling point of the propellant, the container is sealed with a closure equipped with a suitable dispensing valve arrangement. Upon warming to room temperature the contents of the container are mixed by agitation of the container to insure complete solution of the medicament. The sealed container is then ready to dispense the composition and provide the medicament in aerosol form."

Nebulizing units each containing 15 ml. are filled according to the manipulative procedure described above with the following composition:

| | Per cent |
|---|---|
| 2-(3-hydroxy-3-methyl-1-octenyl)-5-oxocyclopentaneheptanoic acid | 0.15 |
| Ethanol | 34.85 |
| Dichlorotetrafluoroethane | 40 |
| Dichlorodifluoromethane | 25 |
| | 100 |

These packages when adjusted to deliver 500 single oral inhalations provide a single dose of 45 micrograms. A single inhalation is administered to control an acute bronchial spasm. If necessary, after a full minute has elapsed, a second inhalation can be administered.

EXAMPLE 9

An injectable unit dosage composition is prepared by dissolving 100 mg. of 2-(3-hydroxy-3-methyl-1-octenyl)-5-oxocyclopentaneheptanoic acid in 30 ml. of 0.2 M sodium phosphate buffer, pH 7.4 and is made up to 100 ml. with distilled water. This solution of medicament, containing 1 mg./ml. of active ingredient (calculated as the free acid) is stored frozen at −20°C. until thawed for sterile filtration. After sterile filtration through a 0.45 micron filter, 1 ml. aliquots are filled aseptically into sterile ampules. The ampules are flame sealed and the contents are frozen and stored at −20°C. until needed.

The subject matter which the applicant regards as his invention is particularly pointed out and distinctly claimed as follows:

1. A chemical compound of the structure

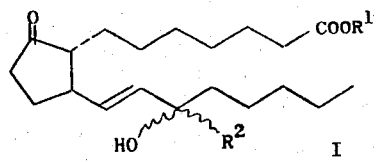

wherein $R^1$ is hydrogen, alkyl of from 1 to 6 carbon atoms, alkali metal, or a pharmacologically-acceptable cation derived from ammonia or a basic amine, and $R^2$ is alkyl of from 1 to about 6 carbon atoms.

2. A compound according to claim 1 wherein $R^2$ is methyl.

3. The compound according to claim 1 wherein $R^1$ is hydrogen and $R^2$ is methyl.

* * * * *